(12) United States Patent
Mower

(10) Patent No.: US 9,789,303 B2
(45) Date of Patent: Oct. 17, 2017

(54) METHOD AND APPARATUS FOR IMPROVED WOUND HEALING

(71) Applicant: Morton M. Mower, Denver, CO (US)

(72) Inventor: Morton M. Mower, Denver, CO (US)

(*) Notice: Subject to any disclaimer, the term of this patent is extended or adjusted under 35 U.S.C. 154(b) by 0 days.

(21) Appl. No.: 14/970,029

(22) Filed: Dec. 15, 2015

(65) Prior Publication Data

US 2016/0175579 A1  Jun. 23, 2016

Related U.S. Application Data

(60) Provisional application No. 62/093,143, filed on Dec. 17, 2014.

(51) Int. Cl.
*A61N 1/04* (2006.01)
*A61N 1/32* (2006.01)
*A61K 9/00* (2006.01)
*A61K 9/70* (2006.01)

(52) U.S. Cl.
CPC .......... *A61N 1/0468* (2013.01); *A61K 9/0009* (2013.01); *A61K 9/703* (2013.01); *A61N 1/0496* (2013.01); *A61N 1/326* (2013.01)

(58) Field of Classification Search
None
See application file for complete search history.

(56) References Cited

U.S. PATENT DOCUMENTS

| 7,477,939 | B2 | 1/2009 | Sun et al. | |
| 2008/0027509 | A1 | 1/2008 | Andino et al. | |
| 2008/0125687 | A1* | 5/2008 | Flick | A61F 13/00063 602/48 |
| 2011/0015697 | A1 | 1/2011 | McAdams | |
| 2012/0237470 | A1* | 9/2012 | Dhal | A61K 31/785 424/78.01 |
| 2013/0316956 | A1* | 11/2013 | Herman | C07K 7/08 514/18.6 |

FOREIGN PATENT DOCUMENTS

WO   2012/125941 A1   9/2012

OTHER PUBLICATIONS

International Search Report and Written Opinion with Search History issued Feb. 26, 2016 in PCT/US2015/065765 filed Dec. 15, 2015.

* cited by examiner

*Primary Examiner* — Ankit D Tejani
(74) *Attorney, Agent, or Firm* — Oblon, McClelland, Maier & Neustadt, L.L.P.

(57) ABSTRACT

A pad for electrically stimulated wound healing, including a pad configured to be placed on a wound, at least one anode disposed on the pad to contact the wound, and at least one cathode disposed on the pad to contact the wound, the at least one cathode being disposed separately from the at least on anode. The pad wherein the at least one anode and the at least one cathode in contact with the wound provide a flow of electrical current in an intended direction through the wound based on the separate locations of the at least one anode and the at least one cathode.

14 Claims, 4 Drawing Sheets

METHOD AND APPARATUS FOR IMPROVED WOUND HEALING

CROSS-REFERENCE TO RELATED APPLICATIONS

This application is based on, and claims the benefit of priority to, provisional application No. 62/093,143, entitled BANDAGE FOR IMPROVED WOUND HEALING and filed Dec. 17, 2014, the entire contents of which are incorporated herein by reference.

BACKGROUND

The "background" description provided herein is for the purpose of generally presenting the context of the disclosure. Work of the presently named inventor, to the extent it is described in this background section, as well as aspects of the description which may not otherwise qualify as prior art at the time of filing, are neither expressly nor impliedly admitted as prior art against the present disclosure.

Care for abrasive skin wounds, skin biopsy sites, and the like typically includes washing the area with peroxide, applying an antibiotic ointment, and covering with a bandage. The bandage can be an adhesive bandage such as a BAND-AID brand bandage with two adhesive portions separated by a gauze portion. Another method of care can involve the application of an electrical current to a skin wound.

It is known that the application of an electrical current to a skin wound can improve healing of the wound. However, the application of an electrical current to the skin can involve the use of a battery and connecting wires. Utilizing a battery and connecting wires can be cumbersome when treating a wound, especially for patients such as ambulatory patients.

SUMMARY

In an exemplary aspect, a pad for electrically stimulated wound healing, including a pad configured to be placed on a wound, at least one anode disposed on the pad to contact the wound, and at least one cathode disposed on the pad to contact the wound, the at least one cathode being disposed separately from the at least one anode. The pad wherein the at least one anode and the at least one cathode in contact with the wound provide a flow of electrical current in an intended direction through the wound based on the separate locations of the at least one anode and the at least one cathode.

The foregoing general description of exemplary implementations and the following detailed description thereof are merely exemplary aspects of the teachings of this disclosure and are not restrictive.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DETAILED DESCRIPTION

Figure 1:
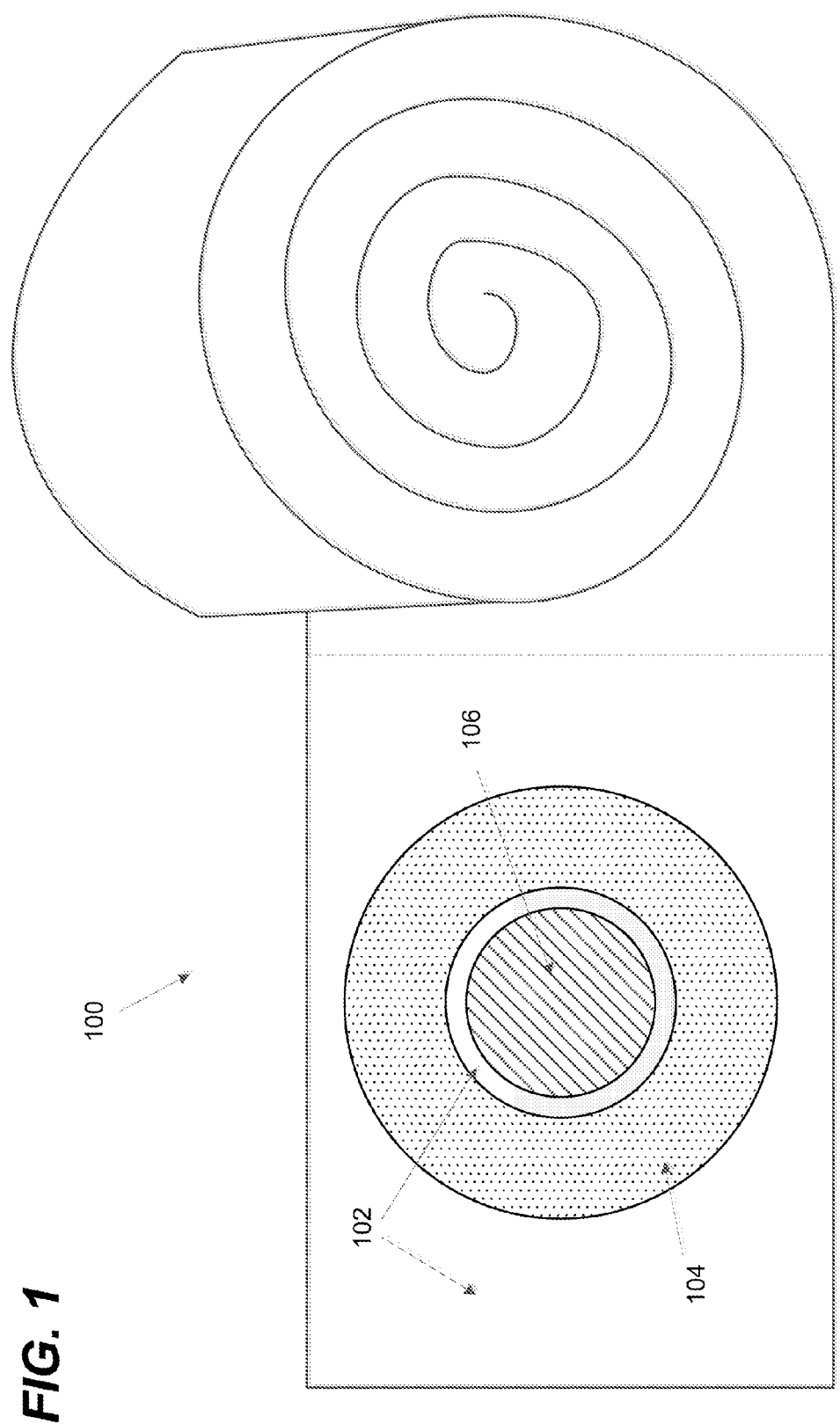
FIG. 1 is an exemplary illustration of a pad including ointments, according to certain aspects.

In the drawings, like reference numerals designate identical or corresponding parts throughout the several views. Further, as used herein, the words "a," "an," and "the" generally carry a meaning of "one or more" or "at least one," unless stated otherwise. Furthermore, the terms "approximately," approximate," "about," and similar terms generally refer to ranges that include the identified value within a margin of 20%, 10%, or preferably 5%, and any values therebetween.

FIG. 1 is an exemplary illustration of a pad including ointments 100, according to certain aspects. The pad including ointments 100 includes a pad 102, an anode 104 and a cathode 106. The pad 102 can include one or more anodes 104 and one or more cathodes 106 located at the pad 102. The pad 102 can be placed at a wound to cover a skin wound, a skin biopsy and the like. The pad 102 can include gauze, mesh, sponge, loose fabric, and any combination of surgical dressings that is known. In certain aspects of the present disclosure, the pad 102 consists of loosely woven cotton and is used as a medical dressing. For example, the pad 102 can be a gauze pad. In another example, the pad 102 can be a roll of gauze with predetermined sections of gauze, in which each section of gauze contains one or more anodes 104 and one or more cathodes 106. The roll of gauze can include perforations to provide a visual aid for a beginning and an end of each desired section. In some aspects, the pad 102 provides a dressing for the wound that does not adhere to the wound itself.

The anode 104 and the cathode 106 are located in separate locations at the pad 102. The anode 104 can be one or more anodes 104 and can be fixed in a particular location at the pad 102. The cathode 106 can be one or more cathodes 106 and can be fixed in a particular location at the pad 102. The anode 104 and the cathode 106 can be placed in contact with a wound to provide a flow of electrical current in an intended direction through the wound. The flow of electrical current can be directed based on the fixed and separate locations of the anode 104 and the cathode 106. The electrical current can flow between the anode 104 and the cathode 106 through the wound. The flow of electrical current through a wound can cause improved healing of the wound due to the application of electrical current to the skin of the wound. For example, the electrical stimulation of the wound, due to the flow of current between the anode 104 and the cathode 106, can cause stem cells of the wound to migrate, divide more readily, and differentiate at a quicker rate to improve healing of the wound.

The anode 104 and the cathode 106 can each include metallic ions. The metallic ions of the anode 104 are dissimilar from the metallic ions of the cathode 106. The anode 104 and the cathode 106 can each be separately deposited as metallic salts in the form two or more distinct topical medications. The topical medications can include ointments, lotions, creams, gels and the like. In certain aspects of the present disclosure, the anode 104 and the cathode 106 are deposited in two distinct ointments. The anode 104 can be deposited in an ointment such as calamine lotion. The calamine lotion can include metallic ions such as zinc oxide and iron oxide. The calamine lotion can include a predetermined quantity of zinc oxide and a predetermined quantity of iron oxide. The cathode 106 can be deposited in an ointment such as 1% silver sulfadiazine cream (SSD).

The ointments, including SSD and calamine lotion, are utilized to promote the flow of electrical current between the metallic ions as a result of the presence of electrolytes in each ointment. Due to the electrolytes present in each of the calamine lotion and the SSD, electrical current can flow between the calamine lotion and the SSD via the wound as the calamine lotion and the SSD are located in distinct locations from one another, separated by an intermediary layer of the pad 302.

The anode 104 and the cathode 106 can be deposited via distinct ointments in the pad 102, on the pad 102, or both. The distinct ointments can be deposited at the pad 102 in locations that are random, symmetric patterns, asymmetric patterns, and the like. For example, the anode 104 can be deposited as a first ointment at the pad 102 in a circular pattern. The cathode 106 can be deposited as a second ointment at the pad in a circular pattern within the inner boundaries of the anode 104. The first ointment and the second ointment can be separated by a circular pattern of pad 102 so that the first ointment and the second ointment are detached from each other. In another example, the anode 104 can be deposited as a first ointment in a line at a first end of the pad 102. The cathode can be deposited as a second ointment in a line at a second end of the pad 102 opposite the first end. The flow of electrical current is then provided when the first ointment and the second ointment come in contact with the wound.

The electrical current can flow between the first ointment and the second ointment via the wound exudate. In some aspects, the electrical current can flow between the first ointment and the second ointment via a metallic wire connecting the first ointment to the second ointment. In other aspects, the electrical current can flow between the first ointment and the second ointment via the first ointment contacting the second ointment. The electrolytes of the first ointment, the electrolytes of the second ointment, the anode 104 of the first ointment, the cathode 106 of the second ointment, and the wound, enable electrical current to flow through the wound, in an intended direction through the wound, between the anode 104 and the cathode 106.

Figure 2:
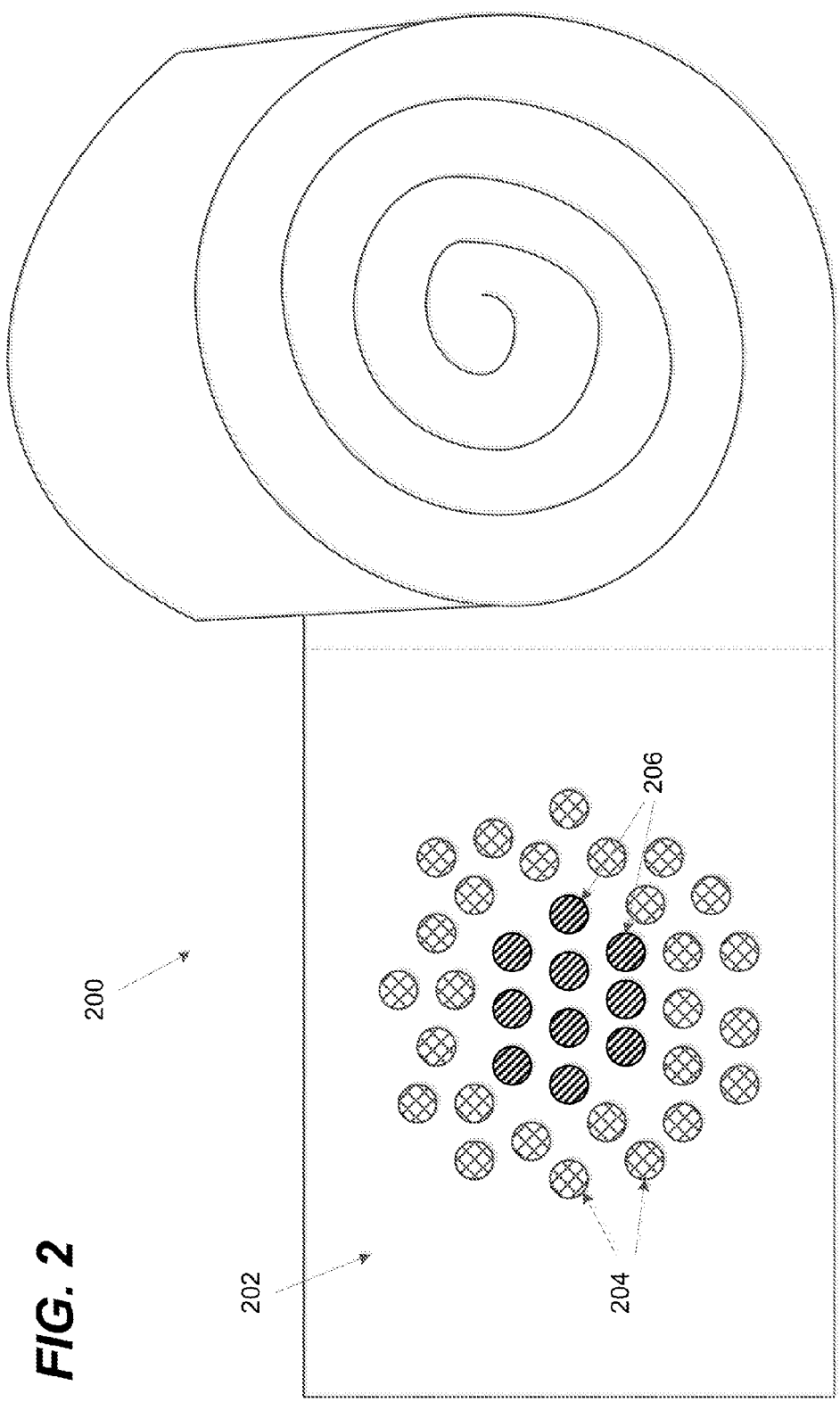
FIG. 2 is an exemplary illustration of a pad including metallic wires, according to certain aspects.

FIG. 2 is an exemplary illustration of a pad including metallic wires 200, according to certain aspects. The pad including metallic wires 200 includes a pad 202, an anode 204 and a cathode 206. The pad 202 can include one or more anodes 204 and one or more cathodes 206 located at the pad 102. The pad 202 can be placed at a wound to cover a skin wound, a skin biopsy and the like. The pad 202 can include gauze, mesh, sponge, loose fabric, and any combination of surgical dressings that is known. In certain aspects of the present disclosure, the pad 202 consists of loosely woven cotton and is used as a medical dressing. For example, the pad 202 can be a gauze pad. In another example, the pad 202 can be a roll of gauze with predetermined sections of gauze, in which each section of gauze contains one or more anodes 204 and one or more cathodes 206. The roll of gauze can include perforations to provide a visual aid for a beginning and an end of each desired section. In some aspects, the pad 202 provides a dressing for the wound that does not adhere to the wound itself.

The anode 204 and the cathode 206 are located in separate locations at the pad 202. The anode 204 can be one or more anodes 206 and can be fixed in a particular location at the pad 202. The cathode 106 can be one or more cathodes 106 and can be fixed in a particular location at the pad 202. The anode 204 and the cathode 206 can be placed in contact with a wound to provide a flow of electrical current in an intended direction through the wound. The flow of electrical current can be directed based on the fixed and separate locations of the anode 204 and the cathode 206. The electrical current can flow between the anode 204 and the cathode 206 through the wound. The flow of electrical current through a wound can cause improved healing of the wound due to the application of electrical current to the skin of the wound. For example, the electrical stimulation of the wound, due to the flow of current between the anode 204 and the cathode 206, can cause stem cells of the wound to migrate, divide more readily, and differentiate at a quicker rate to improve healing of the wound.

The anode 204 and the cathode 206 can each include metallic material. The metallic material of the anode 204 is dissimilar from the metallic material of the cathode 206. The anode 204 and the cathode 206 can each be separately contained in two or more distinct types of metallic wires. In certain aspects of the present disclosure, the anode 204 and the cathode 206 are woven into the pad 202 via two distinct types of metallic wires that are separated by an intermediary layer of the pad 202. The wound can connect the two distinct types of metallic wires via fluids exuding from the surface of the wound. The fluids exuding from the surface of the wound can complete the circuit between the two distinct types of metallic wires and provide a flow of electrical current between the first type of metallic wire(s) containing the anode(s) 204 and the second type of metallic wire(s) containing the cathode(s) 206.

The two types of distinct metallic wires can be woven into the pad 202 in locations that are random, symmetric patterns, asymmetric patterns, and the like. For example, the anode 204 can be provided as a first type of metallic wires at the pad 202 in a circular pattern. The cathode 206 can be provided as a second type of metallic wires at the pad 202 in a circular pattern within the inner boundaries of the anode 204. Each metallic wire of the first type of metallic wires can be separated from one another by portions of the pad 202. As such, each first type of metallic wire is fixed at a distinct location from the other first type of metallic wires. Each metallic wire of the second type of metallic wires can be separated from one another by portions of the pad 202. As such, each second type of metallic wire is fixed at a distinct location from the other second type of metallic wires. Additionally, the first type of metallic wires does not contact the second type of metallic wires directly.

In another example, the anode 204 can be provided as a first type of metallic wires in a line along a length of a first end of the pad 202. The cathode 206 can be provided as a second type of metallic wires in a line along a length of a second end of the pad 202 that is opposite the first end. Each metallic wire of the first type of metallic wires can be separated from one another by portions of the pad 202. As such, each first type of metallic wire is fixed at a distinct location from the other first type of metallic wires. Each metallic wire of the second type of metallic wires can be separated from one another by portions of the pad 202. As such, each second type of metallic wire is fixed at a distinct location from the other second type of metallic wires. The line of the first type of metallic wires is separated from the line of the second type of metallic wires by a portion of the pad 102. The flow of electrical current is then provided when the first type of metallic wires and the second type of metallic wires are both in contact with fluids exuding from the wound, but not in contact with one another. The fluids exuding from the wound, the first type of metallic wires including the anode(s) 204, and the second type of metallic wires including the cathode(s) 206 enable electrical current to flow through the wound in an intended direction through the wound between the anode(s) 204 and the cathode(s) 206.

Figure 3:
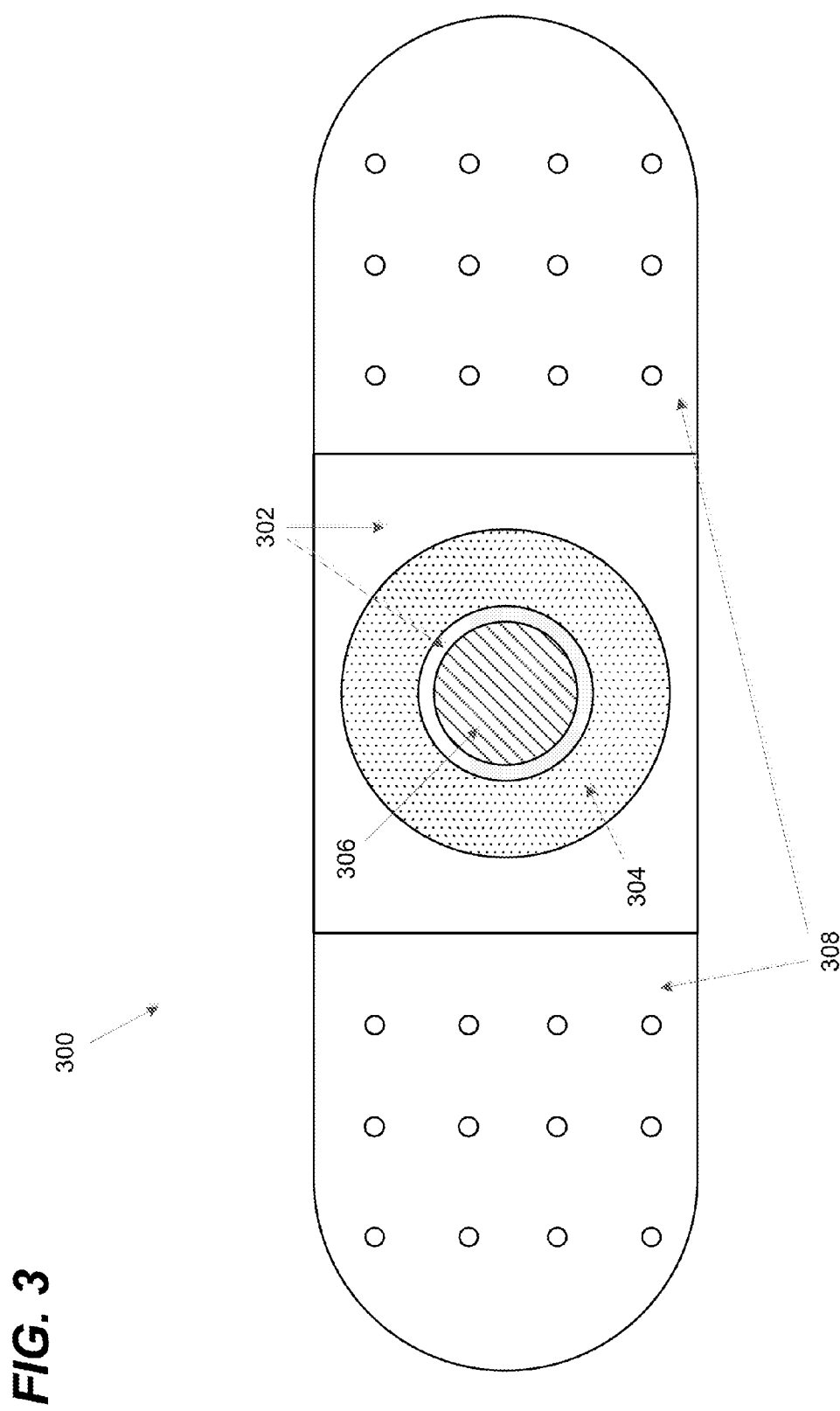
FIG. 3 is an exemplary illustration of an adhesive bandage including ointments, according to certain aspects.

FIG. 3 is an exemplary illustration of an adhesive bandage including ointments 300, according to certain aspects. The adhesive bandage including ointments 300 includes a pad 302, an anode 304, a cathode 306 and an adhesive layer 308. The pad 302 can include one or more anodes 304 and one or more cathodes 306 located at the pad 302. The pad 302 can be attached to at least one adhesive layer 308. The pad 302 can be placed at a wound to cover a skin wound, a skin biopsy and the like. The pad 302 can utilize the adhesive layer 308 to adhere the adhesive bandage including ointments 300 to skin. The pad 302 can include gauze, mesh, sponge, loose fabric, and any combination of surgical dressings that is known. In certain aspects of the present disclosure, the pad 302 consists of loosely woven cotton and is used as a medical dressing. For example, the pad 302 can be a gauze pad. In another example, the pad 302 can be a roll of gauze with predetermined sections of gauze, in which each section of gauze contains one or more anodes 304 and one or more cathodes 306. The roll of gauze can include perforations to provide a visual aid for the beginning and end of each desired section. The pad 302 provides a dressing for the wound and is in direct contact with the wound.

The anode 304 and the cathode 306 are located in separate locations at the pad 302 of the adhesive bandage including ointments 300. The anode 304 can be one or more anodes 304 and can be fixed in a particular location at the pad 302. The cathode 306 can be one or more cathodes 306 and can be fixed in a particular location at the pad 302. The anode 304 and the cathode 306 can be placed in contact with a wound to provide a flow of electrical current in an intended direction through the wound. The flow of electrical current can be directed based on the fixed and separate locations of the anode 304 and the cathode 306. The electrical current can flow between the anode 304 and the cathode 306 through the wound. The flow of electrical current through a wound can cause improved healing of the wound due to the application of electrical current to the skin of the wound. For example, the electrical stimulation of the wound, due to the flow of current between the anode 304 and the cathode 306, can cause stem cells of the wound to migrate, divide more readily, and differentiate at a quicker rate to improve healing of the wound.

The anode 304 and the cathode 306 can each include metallic ions. The metallic ions of the anode 304 are dissimilar from the metallic ions of the cathode 306. The anode 304 and the cathode 306 can each be separately deposited as metallic salts in the form of two or more distinct topical medications. The topical medications can include ointments, lotions, creams, gels and the like. In certain aspects of the present disclosure, the anode 304 and the cathode 306 are deposited in two distinct ointments. The anode 304 can be deposited in an ointment such as calamine lotion. The calamine lotion can include metallic ions such as zinc oxide and iron oxide. The calamine lotion can include a predetermined quantity of zinc oxide and a predetermined quantity of iron oxide. The cathode 306 can be deposited in an ointment such as 1% silver sulfadiazine cream (SSD). The ointments, including SSD and calamine lotion, promote the flow of electrical current between the metallic ions utilizing the presence of electrolytes in each ointment. Due to the electrolytes present in each of the calamine lotion and the SSD, electrical current can flow between the calamine lotion and the SSD via the wound as the calamine lotion and the SSD are located in distinct locations from one another, separated by an intermediary layer of the pad 302.

The anode 304 and the cathode 306 can be deposited via distinct ointments in the pad 302, on the pad 302, or both. The distinct ointments can be deposited at the pad 302 of the adhesive bandage including ointments 300 in locations that are random, symmetric patterns, asymmetric patterns, and the like. For example, the anode 304 can be deposited as a first ointment at the pad 302 in a circular pattern. The cathode 306 can be deposited as a second ointment at the pad 302 in a circular pattern within the inner boundaries of the anode 304. The first ointment and the second ointment can be separated by a circular pattern of pad 302 so that the first ointment is detached from the second ointment. In another example, the anode 304 can be deposited as a first ointment in a line at a first end of the pad 302. The cathode can be deposited as a second ointment in a line at a second end of the pad 302 opposite the first end. The flow of electrical current is then provided when the first ointment and the second ointment come in contact with the wound.

The electrical current can flow between the first ointment and the second ointment via the wound exudate. In some aspects, the electrical current can flow between the first ointment and the second ointment via a metallic wire connecting the first ointment to the second ointment. In other aspects, the electrical current can flow between the first ointment and the second ointment via the first ointment contacting the second ointment. The electrolytes of the first ointment, the electrolytes of the second ointment, the anode 304 of the first ointment, the cathode 306 of the second ointment, and the wound, enable electrical current to flow through the wound, in an intended direction through the wound, between the anode 304 and the cathode 306.

The adhesive layer 308 is attached to the pad 302 and can adhere the adhesive bandage including ointments 300 to skin. The adhesive layer 308 can include a sheet and an adhesive. In some aspects, the adhesive of the adhesive layer 308 is located on one side of the sheet. In other aspects, the adhesive is located on both sides of the sheet. The adhesive can include materials such as acrylate and the like. The sheet can include woven fabric, plastic, a latex strip and the like. Additionally, the adhesive layer 308 can include a removable covering for the side(s) of the adhesive layer 308 that include adhesive. The removable covering can include coated paper, plastic and the like.

In certain aspects of the present disclosure, more than one adhesive layer 308 is attached to the pad 302. For example, a first adhesive layer 308 can attach to a first end of the pad 302 and a second adhesive layer 308 can attach to a second end of the pad 302 opposite the first end. More than one adhesive layer 308 can be utilized to promote the adhering stability of the adhesive bandage including ointments 300 to skin.

Figure 4:
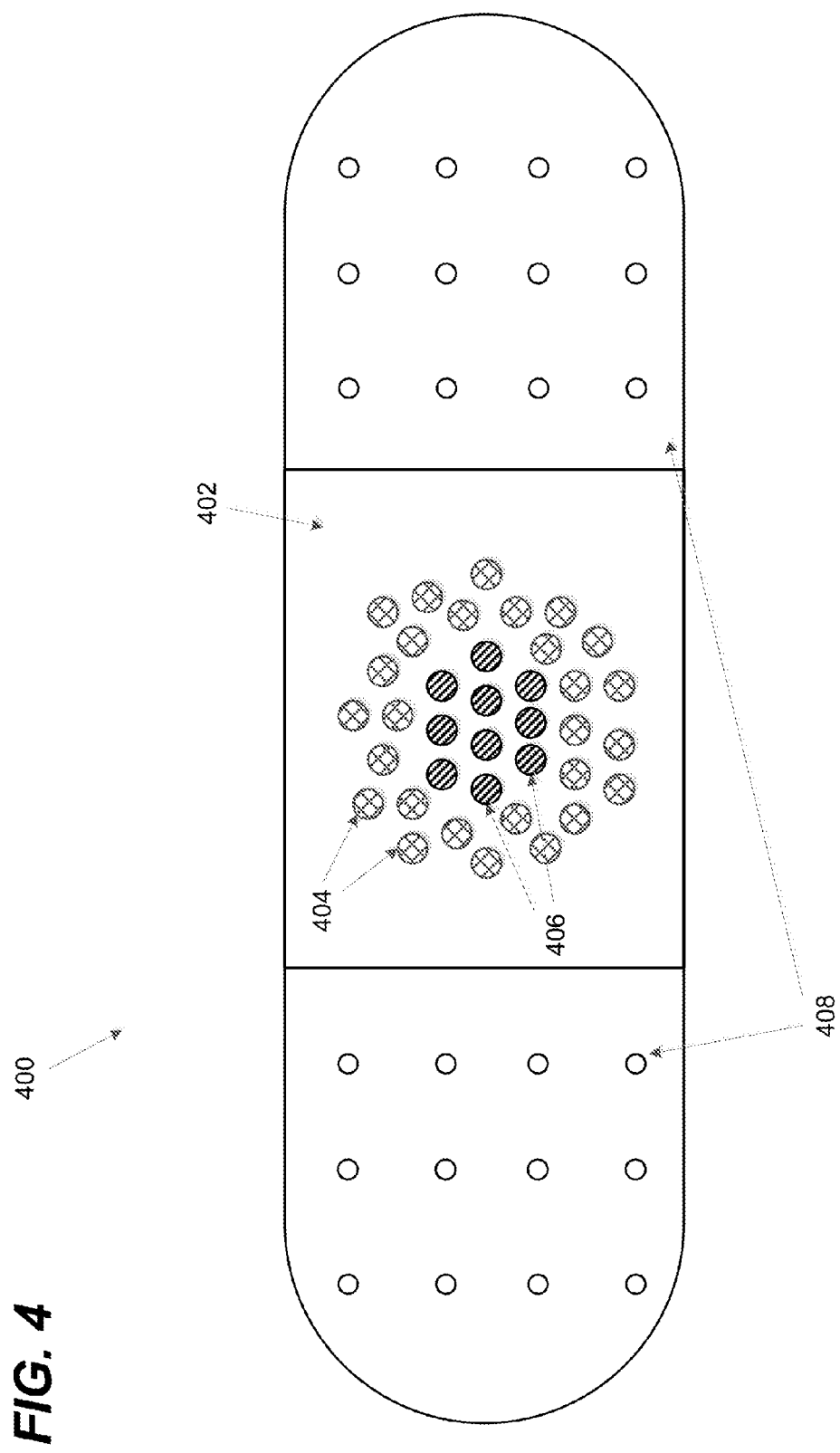
FIG. 4 is an exemplary illustration of an adhesive bandage including metallic wires, according to certain aspects.

FIG. 4 is an exemplary illustration of an adhesive bandage including metallic wires 400, according to certain aspects. The adhesive bandage including metallic wires 400 includes a pad 402, an anode 404, a cathode 406 and an adhesive layer 408. The pad 402 can include one or more anodes 404 and one or more cathodes 406 located at the pad 402. The pad 402 can be attached to at least one adhesive layer 408. The pad 402 can be placed at a wound to cover a skin wound, a skin biopsy and the like. The pad 402 can utilize the adhesive layer 408 to adhere the adhesive bandage including metal wires 400 to skin. The pad 402 can include gauze, mesh, sponge, loose fabric, and any combination of surgical dressings that is known. In certain aspects of the present disclosure, the pad 402 consists of loosely woven cotton and is used as a medical dressing. For example, the pad 402 can be a gauze pad. In another example, the pad 402 can be a roll of gauze with predetermined sections of gauze, in which each section of gauze contains one or more anodes 404 and one or more cathodes 406. The roll of gauze can include perforations to provide a visual aid for a beginning and an end of each desired section. The pad 402 provides a dressing for the wound and is in direct contact with the wound.

The anode 404 and the cathode 406 are located in separate locations at the pad 402 of the adhesive bandage including metallic wires 400. The anode 404 can be one or more anodes 404 and can be fixed in a particular location at the pad 402. The cathode 406 can be one or more cathodes 406 and can be fixed in a particular location at the pad 402. The anode 404 and the cathode 406 can be placed in contact with a wound to provide a flow of electrical current in an intended direction through the wound. The flow of electrical current can be directed based on the fixed and separate locations of the anode 404 and the cathode 406. The electrical current can flow between the anode 404 and the cathode 406 through the wound. The flow of electrical current through a wound can cause improved healing of the wound due to the application of electrical current to the skin of the wound. For example, the electrical stimulation of the wound, due to the flow of current between the anode 404 and the cathode 406, can cause stem cells of the wound to migrate, divide more readily, and differentiate at a quicker rate to improve healing of the wound.

The anode 204 and the cathode 206 can each include metallic material. The metallic material of the anode 204 is dissimilar from the metallic material of the cathode 206. In certain aspects of the present disclosure, the anode 404 and the cathode 406 are woven into the pad 402 via two distinct types of metallic wires that are separated by an intermediary layer of the pad 402. The wound can connect the two distinct types of metallic wires via fluids exuding from the surface of the wound. The fluids exuding from the surface of the wound can complete the circuit between the two distinct types of metallic wires and provide a flow of electrical current between the first type of metallic wire(s) containing the anode(s) 404 and the second type of metallic wire(s) containing the cathode(s) 406.

The two types of distinct metallic wires can be woven into the pad 402 in locations that are random, symmetric patterns, asymmetric patterns, and the like. For example, the anode 404 can be provided as a first type of metallic wires at the pad 402 in a circular pattern. The cathode 406 can be provided as a second type of metallic wires at the pad 402 in a circular pattern within the inner boundaries of the anode 404. Each metallic wire of the first type of metallic wires can be separated from one another by portions of the pad 402. As such, each first type of metallic wire is fixed at a distinct location from the other first type of metallic wires. Each metallic wire of the second type of metallic wires can be separated from one another by portions of the pad 402. As such, each second type of metallic wire is fixed at a distinct location from the other second type of metallic wires. Additionally, the first type of metallic wires does not contact the second type of metallic wires directly.

In another example, the anode 404 can be provided as a first type of metallic wires in a line along a length of a first end of the pad 402. The cathode 406 can be provided as a second type of metallic wires in a line along a length of a second end of the pad 402 opposite the first end. Each metallic wire of the first type of metallic wires can be separated from one another by portions of the pad 402. As such, each first type of metallic wire is fixed at a distinct location from the other first type of metallic wires. Each metallic wire of the second type of metallic wires can be separated from one another by portions of the pad 402. As such, each second type of metallic wire is fixed at a distinct location from the other second type of metallic wires. The line of the first type of metallic wires is separated from the line of the second type of metallic wires by a portion of the pad 402. The flow of electrical current is then provided when the first type of metallic wires and the second type of metallic wires are both in contact with fluids exuding from the wound, but not in contact with one another. The fluids exuding from the wound, the first type of metallic wires including the anode(s) 404, and the second type of metallic wires including the cathode(s) 406 enable electrical current to flow through the wound in an intended direction through the wound between the anode(s) 404 and the cathode(s) 406.

The adhesive layer 408 is attached to the pad 402 and can adhere the adhesive bandage including metallic wires 400 to skin. The adhesive layer 408 can include a sheet and an adhesive. In some aspects, the adhesive of the adhesive layer 408 is located on one side of the sheet. In other aspects, the adhesive is located on both sides of the sheet. The adhesive can include materials such as acrylate and the like. The sheet can include woven fabric, plastic, a latex strip and the like. Additionally, the adhesive layer 408 can include a removable covering for the side(s) of the adhesive layer 408 that include adhesive. The removable covering can include coated paper, plastic and the like.

In certain aspects of the present disclosure, more than one adhesive layer 408 is attached to the pad 402. For example, a first adhesive layer can attach to a first end of the pad 402 and a second adhesive layer can attach to a second end of the pad 402 opposite the first end. More than one adhesive layer 408 can be utilized to promote the adhering stability of the adhesive bandage including metallic wires 400 to skin.

The pad 102 including one or more anodes 104 and one or more cathodes 106, applies an electrical current to a wound to improve the healing of the wound. The pad 102 can include an adhesive layer 302 so that the pad can be applied to the wound as an adhesive bandage 300. The pad 102 provides the benefits of electrical stimulation without the inconvenience of batteries and connecting wires. As such, the pad 102 negates the inconvenience of batteries and connecting wires which has precluded the utilization of wound healing through electrical stimulation. In utilizing the properties of dissimilar metallic ions, as well as properties of the wound itself, the pad 102 provides improved wound healing to treat skin wounds, skin biopsy sites and the like.

The components described can interchangeably be substituted, but are not limited to, the exemplary aspects of the present disclosure. As such, the pad 102 can interchangeably be the pad 202, the pad 302 and/or the pad 402. The anode 104 can interchangeably be the anode 204, the anode 304 and/or the anode 404. The cathode 106 can interchangeably be the cathode 206, 306 and/or the cathode 406. The adhesive layer 308 can interchangeably be the adhesive layer 408.

A number of implementations have been described. Nevertheless, it will be understood that various modifications may be made without departing from the spirit and scope of the present disclosure. For example, preferable results may be achieved if the steps of the disclosed techniques were performed in a different sequence, if components in the disclosed systems were combined in a different manner, or if the components were replaced or supplemented by other components. Accordingly, other implementations are within the scope that may be claimed.

The above disclosure also encompasses the aspects listed below.

(1) A pad for electrically stimulated wound healing, including: a pad configured to be placed on a wound; at least one anode disposed on the pad to contact the wound; and at least one cathode disposed on the pad to contact the wound, the at least one cathode being disposed separately from the at least on anode, wherein the at least one anode and the at least one cathode in contact with the wound provide a flow of electrical current in an intended direction through the wound based on the separate locations of the at least one anode and the at least one cathode.

(2) The pad for electrically stimulated wound healing according to (1), wherein the pad includes at least one of a gauze pad and a gauze roll.

(3) The pad for electrically stimulated wound healing according to either (1) or (2), wherein the at least one anode and the at least one cathode are separately deposited in two or more distinct ointments.

(4) The pad for electrically stimulated wound healing according to any one of (1) to (3), wherein the two or more ointments include silver sulfadiazine cream and calamine lotion.

(5) The pad for electrically stimulated wound healing according to any one of (1) to (4), wherein the silver sulfadiazine cream includes 1% silver sulfadiazine cream.

(6) The pad for electrically stimulated wound healing according to any one of (1) to (5), wherein the calamine lotion includes a predetermined quantity of zinc oxide and a predetermined quantity of iron oxide.

(7) The pad for electrically stimulated wound healing according to any one of (1) to (6), wherein the at least one anode and the at least one cathode are woven into the pad via two or more distinct metallic wires.

(8) An adhesive bandage for electrically stimulated wound healing, including: a pad configured to be placed on a wound; at least one anode disposed on the pad to contact the wound; at least one cathode disposed on the pad to contact the wound, the at least one cathode being disposed separately from the at least on anode, wherein the at least one anode and the at least one cathode in contact with the wound provide a flow of electrical current in an intended direction through the wound based on the separate locations of the at least one anode and the at least one cathode; and at least one adhesive layer attached to the pad and configured to adhere to skin.

(9) The adhesive bandage for electrically stimulated wound healing according to (8), wherein the pad includes at least one of a gauze pad and a gauze roll.

(10) The adhesive bandage for electrically stimulated wound healing according to either (8) or (9), wherein the at least one anode and the at least one cathode are separately deposited in two or more ointments.

(11) The adhesive bandage for electrically stimulated wound healing according to any one of (8) to (10), wherein the two or more ointments include silver sulfadiazine cream and calamine lotion.

(12) The adhesive bandage for electrically stimulated wound healing according to any one of (8) to (11), wherein the silver sulfadiazine cream includes 1% silver sulfadiazine cream.

(13) The adhesive bandage for electrically stimulated wound healing according to any one of (8) to (12), wherein the calamine lotion includes a predetermined quantity of zinc oxide and a predetermined quantity of iron oxide.

(14) The adhesive bandage for electrically stimulated wound healing according to any one of (8) to (13), wherein the at least one anode and the at least one cathode are woven into the pad via two or more distinct metallic wires.

The invention claimed is:

1. A pad for electrically stimulated wound healing, comprising:
    a pad configured to be placed on a wound;
    at least one anode formed of a first material and disposed on the pad to contact the wound; and
    at least one cathode formed of a second material that is different from the first material and disposed on the pad to contact the wound, the at least one cathode being disposed separately from the at least one anode,
    wherein the at least one anode and the at least one cathode in contact with the wound provide a flow of electrical current in an intended direction through the wound based on separate locations of the at least one anode and the at least one cathode, and
    wherein the at least one anode and the at least one cathode provide a flow of electrical current via the exudate of the wound and without a battery and connecting wires.

2. The pad for electrically stimulated wound healing according to claim 1, wherein the pad includes at least one of a gauze pad and a gauze roll.

3. The pad for electrically stimulated wound healing according to claim 1, wherein the at least one anode and the at least one cathode are separately deposited in two or more distinct ointments.

4. The pad for electrically stimulated wound healing according to claim 3, wherein the two or more ointments include silver sulfadiazine cream and calamine lotion.

5. The pad for electrically stimulated wound healing according to claim 4, wherein the silver sulfadiazine cream includes 1% silver sulfadiazine cream.

6. The pad for electrically stimulated wound healing according to claim 4, wherein the calamine lotion includes a predetermined quantity of zinc oxide and a predetermined quantity of iron oxide.

7. The pad for electrically stimulated wound healing according to claim 1, wherein the at least one anode and the at least one cathode are woven into the pad via two or more distinct metallic wires.

8. An adhesive bandage for electrically stimulated wound healing, comprising:
    a pad configured to be placed on a wound;
    at least one anode formed of a first material and disposed on the pad to contact the wound;
    at least one cathode formed of a second material that is different from the first material and disposed on the pad to contact the wound, the at least one cathode being disposed separately from the at least one anode,
    wherein the at least one anode and the at least one cathode in contact with the wound provide a flow of electrical current in an intended direction through the wound based on separate locations of the at least one anode and the at least one cathode,
    at least one adhesive layer attached to the pad and configured to adhere to skin, and
    the at least one anode and the at least one cathode provide a flow of electrical current via the exudate of the wound and without a battery and connecting wires.

9. The adhesive bandage for electrically stimulated wound healing according to claim 8, wherein the pad includes at least one of a gauze pad and a gauze roll.

10. The adhesive bandage for electrically stimulated wound healing according to claim 8, wherein the at least one anode and the at least one cathode are separately deposited in two or more distinct ointments.

11. The adhesive bandage for electrically stimulated wound healing according to claim 10, wherein the two or more ointments include silver sulfadiazine cream and calamine lotion.

12. The adhesive bandage for electrically stimulated wound healing according to claim 11, wherein the silver sulfadiazine cream includes 1% silver sulfadiazine cream.

13. The adhesive bandage for electrically stimulated wound healing according to claim 11, wherein the calamine lotion includes a predetermined quantity of zinc oxide and a predetermined quantity of iron oxide.

14. The adhesive bandage for electrically stimulated wound healing according to claim 8, wherein the at least one anode and the at least one cathode are woven into the pad via two or more distinct metallic wires.

* * * * *

UNITED STATES PATENT AND TRADEMARK OFFICE
CERTIFICATE OF CORRECTION

PATENT NO. : 9,789,303 B2  
APPLICATION NO. : 14/970029  
DATED : October 17, 2017  
INVENTOR(S) : Morton M. Mower Page 1 of 1

It is certified that error appears in the above-identified patent and that said Letters Patent is hereby corrected as shown below:

On the Title Page

In the Abstract, Line 6, change "on" to --one--.

In the Specification

Column 2, Line 57, change "form two" to --form of two--.

Signed and Sealed this  
Ninth Day of October, 2018

Andrei Iancu  
*Director of the United States Patent and Trademark Office*